United States Patent [19]

Nakagawa et al.

[11] Patent Number: 4,792,615

[45] Date of Patent: Dec. 20, 1988

[54] METHOD OF PRODUCING α-DIHYDROPOLYPRENYL MONOPHOSPHATES

[76] Inventors: Naoshi Nakagawa, 2282; Tetsuo Takigawa, 160-4, Bakuro-cho; Akira Kageyu, 2047-1, all of Kurashiki; Michiya Shimamura, 594-2, 1-chome, Natsumi-cho, Funabashi; Masafumi Okada, 1652; Masao Mizuno, 335-18, both of Kurashiki, all of Japan

[21] Appl. No.: 429

[22] Filed: Dec. 22, 1986

[30] Foreign Application Priority Data

Dec. 20, 1985 [JP] Japan .................................. 60-288688
Dec. 27, 1985 [JP] Japan .................................. 60-297941

[51] Int. Cl.$^4$ .............................................. C07F 9/09
[52] U.S. Cl. .................................................. 558/144
[58] Field of Search .............................. 558/101, 144

[56] References Cited

U.S. PATENT DOCUMENTS 3,236,920  2/1966  Hems et al. ......................... 558/101

OTHER PUBLICATIONS

Danilov et al., "FEBS Letters", vol. 131, No. 2 (1981), pp. 310–312.

Primary Examiner—Anton H. Sutto
Attorney, Agent, or Firm—Burns, Doane, Swecker & Mathis

[57] ABSTRACT

A method of producing α-dihydropolyprenyl monophosphates from α-dihydropolyprenols through α-dihydropolyprenyl dichlorophosphates in good yield and with ease is provided. A method of producing α-dihydropolyprenyl dichlorophosphates which are intermediate compounds useful for the first-mentioned method is also provided.

5 Claims, No Drawings

METHOD OF PRODUCING α-DIHYDROPOLYPRENYL MONOPHOSPHATES

BACKGROUND OF THE INVENTION

1. Field of the Invention

The present invention relates to a method of producing α-dihydropolyprenyl monophosphates and a method of producing α-dihydropolyprenyl dichlorophosphates which are intermediate compounds useful therefor.

2. Description of the Prior Art

There are known several methods for synthesizing α-dihydropolyprenyl monophosphates using α-dihydropolyprenols as starting compounds. Thus, several methods are known for synthesizing a dolichyl monophosphate [hereinafter referred to as dolichyl monophosphate (I')]of the general formula $$CH_3-\underset{\underset{CH_3}{|}}{C}=CH-CH_2+CH_2-\underset{\underset{H}{|}}{\overset{\overset{CH_3}{|}}{C}}=\underset{}{C}-CH_2)_2+CH_2-\underset{\underset{H}{|}}{\overset{\overset{H_3C}{|}}{C}}=\underset{}{C}-CH_2)_{\overline{n}}CH_2-\underset{\underset{}{|}}{\overset{\overset{CH_3}{|}}{C}}H-CH_2-CH_2-O-\underset{\underset{OH}{\backslash}}{\overset{\overset{O}{\parallel}}{P}}\overset{OH}{/} \quad (I')$$

from a dolichol [hereinafter referred to as dolichol (II')-]of the general formula $$CH_3-\underset{\underset{CH_3}{|}}{C}=CH-CH_2+CH_2-\underset{\underset{H}{|}}{\overset{\overset{CH_3}{|}}{C}}=C-CH_2)_2+CH_2-\underset{\underset{H}{|}}{\overset{\overset{H_3C}{|}}{C}}=C-CH_2)_{\overline{n}}CH_2-\overset{\overset{CH_3}{|}}{C}H-CH_2-CH_2-OH \quad (II')$$

wherein $\overset{CH_3}{\overset{|}{-}}$ means a trans-isoprene unit $$-CH_2-\underset{\underset{H}{|}}{\overset{\overset{CH_3}{|}}{C}}=C-CH_2-$$

and means a cis-isoprene unit; n means $$-CH_2-\overset{\overset{H_3C}{|}}{C}=\overset{\overset{H}{|}}{C}-CH_2$$

an integer of 12 to 18.

Among these known methods are the method of Warren and Jeanloz in which bis(triethylammonium) hydrogen phosphate is used in the presence of trichloroacetonitrile [Biochemistry 14, 412 (1975)], the method of L. L. Danilov and T. Chojnacki in which phosphoryl chloride is used [FEBS Lett., 131, 130 (1981)]; the method of Rupar and K. K. Carroll in which there is used a phosphoryl chloride derivative of the formula (IV)

which is the product of partial substitution of P-Cl bonds of phosphoryl chloride [Chem. Phys. Lipids, 17, 193 (1976)]; and the method of Warren and Jeanloz in which there is used a phosphoryl chloride derivative of the formula (V)

[hereinafter referred to as phosphoryl chloride derivative (V)][Methods Enzym., 50, 122 (1978)].

Among these known methods, the method using bis(triethylammonium) hydrogen phosphate in the presence of trichloroacetonitrile has the disadvantage that dolichyl pyrophosphate which cannot be easily separated from dolichyl monophosphate (I') is inevitably by-produced and, therefore, this method is not suitable for the commercial production of dolichyl monophosphate (I'). The method using the phosphoryl chloride derivative (IV) is disadvantageous in that the reaction conditions for the production of compound (IV) are so critical that the compound (IV) cannot be readily available. The method using phosphoryl chloride derivative (V) has the disadvantage that in the step where the coupling reaction product from dolichol (II') is hydrolyzed to dolichyl monophosphate (I'), the unstable and toxic reagent lead tetraacetate must be employed. Thus, these methods cannot be practiced for the commercial production of dolichyl monophosphates (I') which are to be used in medicinal applications as described hereinafter. On the other hand, according to the literature referred to above, the method using phosphoryl chloride was used in the synthesis of dolichyl monophosphate (I') from a small quantity, say 40 mg or less, of dolichol (II'). When the present inventors applied the above method using phosphoryl chloride to 50 g of dolichol (II'), it was found that along with the formation of the desired product dolichyl monophosphate (I'), an impurity of low polarity which, in thin layer chromatography (TLC), is developed farther beyond the spot of dolichyl monophosphate (I') is by-produced. This TLC analysis was made using Merck's TLC Plate No. 5715 and, as a developing solvent system, a 65:25:4 (v/v) mixture of chloroform, methanol and water. Thus, the chromatogram showed dolichyl monophosphate (I') at Rf=0.50 and the above impurity at Rf=0.63. In order to remove this impurity, attempts were made to purify the reaction product by silica gel column chromatography, reversed-phase silica gel column chromatography, diethylaminoethylcellulose (DEAEcellulose) column chromatography, preparative thin layer chromatography and so on, but it was impossible to completely remove the impurity As a method comprising reacting an alcohol with phosphoryl chloride to give the corresponding dichlorophosphate, there is known the process in which 6-hydroxyhexyl methacrylate was reacted with phosphoryl chloride in diethyl ether in the presence of triethylamine [U.S. Pat. No. 4,515,930]. This reaction is conducted at −50° C. and the reaction condition thereof as such is not industrially practical. As a matter of fact, when this reaction condition was applied to α-dihydropolyprenol for the production of α-dihydropolyprenyl monophosphate, the desired α-dihydropolyprenyl monophosphate was not advantageously obtained as shown in Reference Example 12 mentioned hereinafter.

It is an object of the present invention to provide a commercially advantageous method of producing an α-dihydropolyprenyl monophosphate in good yield and with ease from an α-dihydropolyprenol without inducing an appreciable by-production of hardly separable impurities such as the above-mentioned one.

It is another object of the present invention to provide a method of producing an α-dihydropolyprenyl dichlorophosphate, which can be easily converted to an α-dihydropolyprenyl monophosphate in good yield, from an α-dihydropolyprenol with facility and in good yield.

These objects as well as other objects and advantages of the present invention will become apparent to those skilled in the art from the following detailed description.

SUMMARY OF THE INVENTION

In accordance with the present invention, there is provided a method of producing an α-dihydropolyprenyl monophosphate of the general formula (I) [which will hereinafter be referred to as α-dihydropolyprenyl monophosphate (I)]

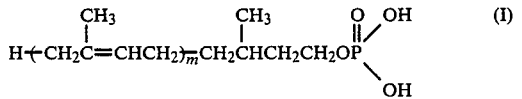

wherein m is an integer of 4 to 22 which comprises reacting an α-dihydropolyprenol of the general formula (II) [which will hereinafter be referred to as α-dihydropolyprenol (II)]

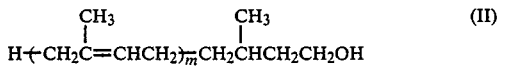

wherein m is as defined above with phosphoryl chloride in an ethereal solvent in the presence of a basic compound to give an α-dihydropolyprenyl dichlorophosphate of the general formula (III) [which will hereinafter be referred to as α-dihydropolyprenyl dichlorophosphate (III)]

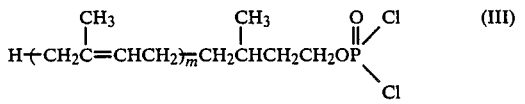

wherein m is as defined above and, then, hydrolyzing the obtained α-dihydropolyprenyl dichlorophosphate (III) with an alkali metal hydroxide or alkaline earth metal hydroxide in an ethereal solvent.

In accordance with the present invention, there is further provided a method of producing said α-dihydropolyprenyl dichlorophosphate (III) from the α-dihydropolyprenol (II).

DETAILED DESCRIPTION OF THE INVENTION

In accordance with the present invention, the α-dihydropolyprenyl dichlorophosphate (III) can be produced by reacting an α-dihydropolyprenol (II) with phosphoryl chloride in an ethereal solvent in the presence of a basic compound.

The ethereal solvent used in this reaction is exemplified by tetrahydrofuran, 1,2-dimethoxyethane, diethyl ether (hereinafter referred to briefly as THF, DME and ether, respectively), diethylene glycol dimethyl ether, 1,2-diethoxyethane, 1,4-dioxane and so on. Among these solvents, THF, DME and ether are convenient solvents. The amount of the solvent is about 2 to 100 times by weight, preferably about 4 to 10 times by weight, based on α-dihydropolyprenol (II). The basic compound is preferably a tertiary amine such as trimethylamine, triethylamine, pyridine, etc. and the use of triethylamine, pyridine, etc. is expedient. The amount of said basic compound is about 1 to 50 molar equivalents, preferably about 1.5 to 5 molar equivalents per mole of α-dihydropolyprenol (II). The amount of phosphoryl chloride is about 1 to 100 molar equivalents, preferably about 2 to 10 molar equivalents per mole of α-dihydropolyprenol (II). Generally, the reaction is preferably conducted at temperatures of about 0° to 10° C. While the reaction time varies with the reaction temperature used, it is generally about 0.5 to 2 hours. A preferred mode of this reaction is as follows. A mixed solution of α-dihydropolyprenol (II) and triethylamine in THF is added dropwise to phosphoryl chloride under ice-cooling with the reaction mixture being maintained at a temperature below 10° C. and after completion of the dropwise addition, the reaction mixture is stirred under ice-cooling for 2 hours.

After completion of the reaction, the reaction mixture containing the product α-dihydropolyprenyl dichlorophosphate (III) may be directly subjected to the next hydrolysis reaction or, alternatively, the α-dihydropolyprenyl dichlorophosphate (III) is separated from the reaction mixture by the conventional method and then subjected to the hydrolysis reaction. Separation of α-dihydropolyprenyl dichlorophosphate (III) from the reaction mixture is generally carried out as follows. The reaction mixture is concentrated under reduced pressure and the concentrate is suspended in ether. This suspension is filtered and the filtrate is concentrated.

The ethereal solvent that is used in the hydrolysis reaction according to the present invention is exemplified by THF, DME, ether, diethylene glycol dimethyl ether, 1,2-diethoxyethane, 1,4-dioxane and so on. In view of availability and ease of use, THF, DME and ether are preferred. The amount of the solvent is about 2 to 100 times by weight, preferably about 4 to 10 times by weight, based on α-dihydropolyprenyl dichlorophosphate (III). The alkali metal hydroxide mentioned hereinbefore is exemplified by sodium hydroxide, potassium hydroxide and so on, and the alkaline earth metal hydroxide is exemplified by barium hydroxide, calcium hydroxide and the like. The amount of such alkali metal hydroxide or alkaline earth metal hydroxide is about 2 to 10 molar equivalents, preferably about 3 to 4 molar equivalents per mole of α-dihydropolyprenyl dichlorophosphate (III). Generally, this reaction is preferably conducted at temperatures of about 0 to 10° C. While the reaction time varies with the reaction temperature used, the reaction generally goes to completion in about 2 to 15 hours.

After completion of the reaction, the product α-dihydropolyprenyl monophosphate (I) can be separated from the reaction mixture and purified by the procedure known per se. For example, the reaction mixture is extracted with an equal volume of chloroform 3 times and the organic layers are pooled and dried over anhydrous calcium chloride. The dried organic solution is then filtered with the aid of Celite and the filtrate is concentrated under reduced pressure to give crude α-dihydropolyprenyl monophosphate (I). This crude product is subjected to DEAE-cellulose column chromatography [eluent: a 20:10:1 (v/v) mixture of chloroform, methanol and water; gradient: ammonium acetate from 0 to 30 mM]and the fractions containing α-dihydropolyprenyl monophosphate (I) only [as found by TLC]are combined and concentrated under reduced pressure. To this concentrate is added chloroform and the mixture is stirred well and filtered with the aid of Florisil. The filtrate is then concentrated to give pure α-dihydropolyprenyl monophosphate (I).

Among the α-dihydropolyprenols (II) that can be used as starting compounds in the practice of the present invention, dolichol (II') can be easily prepared as a mixture of homologs having the undermentioned molecular weight distribution by the method described in Japanese Patent Publication (unexamined) No. 58-83643.

| Number of cis-isoprene units (n) | Relative amount (%) |
|---|---|
| 12 | 0.1–6 |
| 13 | 4–17 |
| 14 | 20–35 |
| 15 | 30–50 |
| 16 | 10–25 |
| 17 | 2–10 |
| 18 | 0.1–5 |

If necessary, the above mixture may be fractionated by molecular weight and one of the homologs be used as the starting material in the practice of the present invention. It is also possible to use a mixture consisting of two or more such homologs in optional proportions. It is further possible to prepare an α-dihydropolyprenol from a polyprenol having a suitable number of isoprene units or a mixture of such polyprenols in accordance with the method described in the above patent literature and use the α-dihydropolyprenol as the starting material in the practice of the present invention.

Among the α-dihydropolyprenyl monophosphate (I) produced by the method of the present invention, the α-dihydropolyprenyl monophosphates of the general formula (I) wherein m is equal to 15 to 22 are known to be widely distributed in the bodies of mammals, where they are acting as rate-determining factors in the synthesis of glycoproteins which play very important roles in the maintainance of life. These compounds are also useful as drugs such as liver function enhancement agents, antiinflammatory agents, immunological enhancement agents and so on. Furthermore, the α-dihydropolyprenyl monophosphate of the general formula (I) wherein m is equal to 9 is known to be a compound of value as an antineoplastic agent (Japanese Patent Publication (unexamined) No. 60-67424].

Moreover, α-dihydropolyprenyl dichlorophosphates (III) can be converted to useful dolichyl glycopyranosyl phosphates of the general formula (VI) [which are hereinafter referred to briefly and collectively as phosphate (VI)]

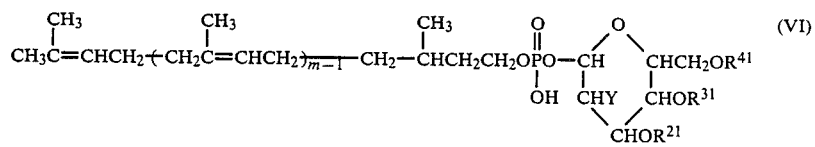

wherein m is as defined hereinbefore; Y is a hydrogen atom, an acetamido group or $OR^{11}$; $R^{11}$, $R^{21}$, $R^{31}$ and $R^{41}$ may be the same or different and each is $-COQ^{11}$ or $-Q^{21}$ where $Q^{11}$ is a lower alkyl group or an aryl group and $Q^{21}$ is a hydrogen atom, a lower alkyl group, an aryl group or an aralkyl group. The like symbols have the like meanings in this specification. And among such phosphates (VI), dolichyl glycopyranosyl phosphates of the general formula (VI') [which are hereinafter referred to briefly and collectively as phosphate (VI')].

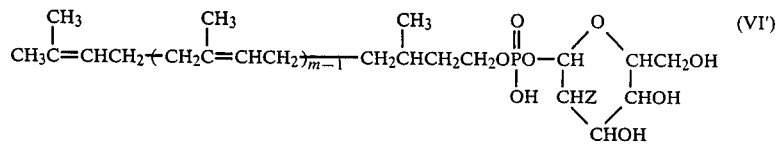

wherein Z is a hydrogen atom, an acetamido group or a hydroxyl group are important substances which are utilized as sugar constituents in the biosynthesis of glycoproteins being necessary for the growth of the body and the maintenance of life. Moreover, phosphates (VI) other than phosphates (VI') are useful materials for the production of phosphates (VI'). For example, dolichyl mannopyranosyl phosphate, dolichyl glucopyranosyl phosphate and dolichyl galactopyranosyl phosphate are known to serve as substrates for glycosyltransferase in the biosynthesis of dolichyl diphosphate oligosaccharides which are important intermediates in the biosynthesis of glycoproteins and be taken up into glycoproteins [A. J. Parodi; and L. F. Leloir, Biochim. Biophys. Acta, 1979, 559, 1 and its references]. Dolichyl 2-deoxyglucopyranosyl phosphate is said to be taken up into glycoproteins in yeast body to inhibit saccharification of the resulting glycoproteins [L. Lehle and R. T. Schwarz, Eur. J. Biochem., 1796, 67, 239]. Further, dolichyl mannopyranosyl phosphate is known to have antineoplastic activity [Japanese Patent Publication (unexamined) No. 59-155319].

Phosphates (VI) can be produced by the following and other methods. For example, an α-dihydropolyprenyl dichlorophosphate (III) is condensed with a glucopyranose derivative of the general formula (VII) [which is hereinafter referred to briefly as pyranose (VII)]

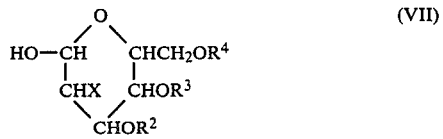

wherein X is a hydrogen atom, an acetamido group or $OR^1$; $R^1$, $R^2$, $R^3$ ans $R^4$ may be the same or different and each is $-COQ^1$ or $-Q^2$, where $Q^1$ is a lower alkyl group or an aryl group and $Q^2$ is a lower alkyl group, an aryl group or an aralkyl group [The same applies hereinunder] in the presence of a basic substance and the resulting condensation product is hydrolyzed to give a dolichyl glucopyranosyl phosphate derivative of the general formula (VI″) [which is hereinafter referred to as phosphate derivative (VI″)]

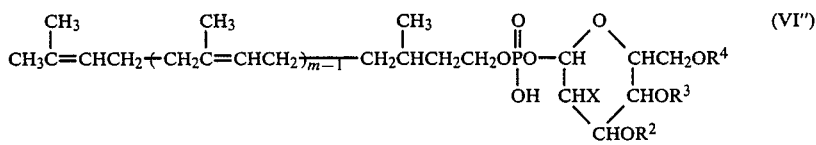

wherein m, X, $R^2$, $R^3$ and $R^4$ are as defined hereinbefore. If necessary, this phosphate derivative (VI″) is subjected to solvolysis or dissolving metal reduction. In the above reaction procedure, said α-dihydropolyprenyl dichlorophosphate (III) and pyranose (VII) are used in a molar ratio of about 1:20 through 5:1, preferably about 1:2 through 2:1. The basic substance used in this reaction is exemplified by organolithium compounds such as n-butyllithium, sec-butyllithium, tert-butyllithium, methyllithium, phenyllithium, etc.; metal hydrides such as sodium hydride, potassium hydride, lithium hydride, etc.; and metal amides such as lithium hexamethyldisilazide, sodium hexamethyldisilazide, lithium tetramethylpiperazide, etc. From the standpoint of the ease of handling and availability, n-butyllithium and sodium hydride are preferably used. The amount of said basic substance is about 0.8 to 2 equivalents, preferably about 0.95 to 1.2 equivalents, per mole of pyranose (VII). This reaction is preferably conducted in the presence of a solvent. As the solvent that can be used, there may be mentioned aprotic solvents such as ethereal solvents, e.g. THF, ether, dimethoxyethane, 1,4-dioxane, etc., and hydrocarbon solvents such as benzene, toluene, xylene, hexane, pentane and so on. From the standpoint of availability, ease of use, etc., THF and ether are preferred. The amount of the solvent, though not critical, is about 1 to 100 times by weight, preferably about 2 to 15 times by weight, based on α-dihydropolyprenyl dichlorophosphate (III). In addition, as a co-solvent, an amine compound such as hexamethylphosphoric triamide [hereinafter referred to as HMPA], tetramethylethylenediamine, 1,3-dimethyl-2imidazolidinone, triethylenediamine, etc. may be used in a proportion of about 1 to 3 equivalents per mole of pyranose (VII). Generally, the reaction is preferably conducted at temperatures of about $-100°$ C. to $0°$ C. While the reaction time is dependent on the reaction temperature used, it is generally about 2 to 24 hours. A preferred mode of this reaction is as follows. In an inert atmosphere, n-butyllithium is added dropwise to a solution of pyranose (VII) in THF at a temperature of $-70$ to $-60°$ C. Then, a solution of α-dihydropolyprenyl dichlorophosphate (III) in THF is added at the same temperature, followed by addition of HMPA. The mixture is further stirred at $-70$ to $-60°$ C for 12 hours.

After completion of the reaction, the reaction mixture containing the condensation product may be directly subjected to the next hydrolysis reaction or, alternatively, the condensation product is separated from the reaction mixture and subjected to the hydrolysis reaction. Separation of the condensation product from the reaction mixture can be accomplished in the same manner as separation of reaction products in general organic synthesis. For example, the reaction mixture is poured in water and extracted with an organic solvent such as ether, chloroform or the like. The organic layer is dried, the solvent is distilled off, and the residue is fractionated by column chromatography to isolate the condensation product.

The condensation product thus obtained may be represented by the general formula

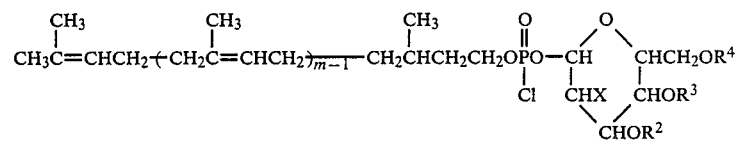

wherein m, X, $R^2$, $R^3$ and $R^4$ are as defined hereinbefore, and is a novel compound that has not been described in the literature.

The hydrolysis reaction is carried out in the presence of a basic substance. The basic substance is preferably an organic amine or an alkali metal hydroxide or alkaline earth metal hydroxide. Examples of the organic amine are tertiary amines such as pyridine, triethylamine and so on. Examples of the alkali metal hydroxide include sodium hydroxide, potassium hydroxide and so on. The alkaline earth metal hydroxide may be barium hydroxide, calcium hydroxide or the like. The organic amine, alkali metal hydroxide or alkaline earth metal hydroxide is used in a proportion of about 1 to 5 equivalents, preferably 1.1 to 2 equivalents, per mole of α-dihydropolyprenyl dichlorophosphate (III). This reaction is preferably conducted in a solvent. The solvent may be an ethereal solvent such as THF, ether or the like. The amount of the solvent is not critical and may be about 1 to 100 times by weight, preferably about 2 to 15 times by weight, based on α-dihydropolyprenyl dichlorophosphate (III). Generally, this reaction is preferably conducted at temperatures of about $-20°$ C. to $20°$ C. While the reaction time is dependent on the reaction temperature used, the reaction is generally completed in about 1 to 15 hours.

After completion of the reaction, the phosphate derivative (VI″) can be separated from the reaction mixture by procedures similar to those used commonly in separating reaction products in general organic synthesis. For example, the organic layer of the reaction mixture is separated and the aqueous layer is extracted with an organic solvent such as ether, chloroform or the like. The organic layers are combined and dried, followed by removal of the solvent. The distillation residue is then fractionated by column chromatography to isolate the phosphate derivative (VI″).

If necessary, this phosphate derivative (VI″) can be subjected to solvolysis or dissolving metal reduction to give a phosphate (VI). Thus, when the phosphate derivative (VI″) has a lower alkanoyl group, e.g. acetyl, or an aroyl group, e.g. benzoyl, as a protective group of a hydroxyl group, this phosphate derivative (VI″) can be subjected to solvolysis such as hydrolysis, alcoholysis, etc. to give the phosphate (VI′). When the phosphate derivative (VI″) has an aralkyl group, e.g. benzyl, as a protective group of a hydroxyl group, it can be subjected to dissolving metal reduction to give the phosphate (VI′).

The hydrolysis mentioned above is generally conducted in the presence of an alkaline substance. As the alkaline substance, an alkali metal hydroxide such as lithium hydroxide, sodium hydroxide, potassium hydroxide, etc. may be employed. This reaction can be conducted in the concomitant presence of a co-solvent such as THF, chloroform or the like. Generally, this reaction is preferably conducted at temperatures of about 0 to 20° C. and goes to completion in about 1 to 12 hours, depending on the reaction temperature used. The alcoholysis mentioned above is generally carried out in the presence of a metal alkoxide. The alcohol used for this reaction may for example be methanol or ethanol, and the metal alkoxide is exemplified by sodium methoxide, sodium ethoxide and so on. The metal alkoxide is generally used as an about 0.5 to 5% solution in the corresponding alcohol and added in an amount such that the pH of the reaction mixture is rendered strongly alkaline (pH 12 or more). This reaction can be conducted in the concomitant presence of a co-solvent such as chloroform or the like. Generally this reaction is preferably conducted at temperatures of about −20° C. to 20° C. and goes to completion in about 30 minutes to 10 hours, depending on the reaction temperature used. The dissolving metal reduction is carried out by using an alkali metal such as lithium, sodium, etc. to act in ammonia or an amine such as methylamine, ethylamine or the like. For this reaction, an organic solvent such as THF, ether or the like may be used as a co-solvent. Generally this reaction is preferably conducted at temperatures of about −50° C. to 0° C. and goes to completion in about 1 to 10 hours, depending on the temperature used. The separation and purification of the phosphate (VI′) after the abovementioned reactions can be accomplished by the separation and purification procedures well known in the art of organic synthesis.

The starting material pyranose (VII) can be easily prepared by the known method. For example, the two anomers of 2,3,4,6-tetra-0-acetylmannopyranose can be produced from commercial mannose in accordance with the methods of Bonner and Warren et al [W. A. Bonner: J. Am. Chem. Soc., 1958, 80, 3372 and C. D. Warren et al.: J. Biol. Chem., 1975, 250, 8069]. The two anomers of 2,3,4,6-tetra-0-acetylglucopyranose can be produced from commercial glucose in accordance with any of the method of Wolfrom et al, the method of Bollenback et al, and the method of Allen [M. L. Wolfrom and A. Thompson: Methods Carbohydr. Chem., 1963, 2, 212; G. N. Bollenback et al.: J. Am. Chem. Soc., 1955, 77, 3310; and P. Z. Allen: Methods Carbohydr. Chem., 1963, 2, 372]. Further, 2,3,4,6-tetra-0-benzylmannopyranose and 2,3,4,6-tetra-0-benzylglucopyranose can be prepared from commercial methyl mannopyranoside or commercial methyl glucopyranoside, respectively, in accordance with the method of Koto et al [S. Koto et al.: Bull. Chem. Soc. Japan, 1976, 49, 2639].

As will be apparent from the working examples given hereinafter, the method according to the present invention enables one to produce α-dihydropolyprenyl monophosphate (I) from an α-dihydropolyprenol (II) in good yield, with ease, and in high purity. Furthermore, the method enables one to obtain high-pure α-dihydropolyprenyl monophosphates (I) on a large production scale, thus being suitable for the commercial production of α-dihydropolyprenyl monophosphates (I).

EXAMPLES

The present invention will be described in further detail by way of working examples, it being to be understood that the invention is by no means limited to these examples. In the examples, $^1$H-NMR spectra were recorded as $CDCl_3$ solution with tetramethylsilane as an internal standard and IR spectra were determined as films.

REFERENCE EXAMPLE 1

The phosphorylation of dolichol was carried out according to the method of L. L. Danilov and T. Chojnacki on about 1,000 times larger scale than by their method. The dolichol used as the starting material was a mixture of homologs of the general formula (II′) wherein n means an integer of 12 to 18. The composition of the above dolichol was as follows.

| Number of cis-isoprene units (n) | Relative amount (%) |
| --- | --- |
| 12 | 1.5 |
| 13 | 7.4 |
| 14 | 27.1 |
| 15 | 37.6 |
| 16 | 17.8 |
| 17 | 6.4 |
| 18 | 2.2 |

An argon-purged three-necked flask was charged with 1 liter of distilled hexane and with stirring at room temperature, 19.2 ml (206 m mol) of phosphoryl chloride was added followed by addition of 28.7 ml (206 m mol) of triethylamine. A solution of 50 g (38 m mol) of dolichol in 2 liters of distilled hexane was added thereto dropwise. Following the addition, the mixture was further stirred for 15 minutes. The reaction mixture was then poured into 10 liters of a 88:10:2 (v/v) mixture of acetone, water and triethylamine, followed by stirring for 18 hours. The mixture was then concentrated under reduced pressure on a rotary evaporator. To the concentrate was added 3 liters of n-propanol and the mixture was concentrated similarly. With the addition of 5 liters of benzene, the residue was concentrated in the same manner as above. The concentration with addition of 2 liters of benzene was repeated until crystals separated out. To the concentrate was added 2 liters of benzene and the mixture was stirred well and then allowed to stand for 1 hour. The crystals were filtered off and the filtrate was concentrated to dryness. The concentrate was dissolved in a 2:1 (v/v) mixture of chloroform and methanol and submitted to column chromatography [column: DEAEcellulose, Whatman DE-52, acetate-form, 3.5 cm(dia.) × 125 cm; eluent: chloroform-methanol=2:1, v/v; gradient: ammonium acetate from 0 to 45 mM]. The fractions rich in dolichyl monophosphate as detected by TLC analysis were collected and concentrated under reduced pressure. The concentrate was dissolved in a 2:1 (v/v) mixture of chloroform and methanol and submitted to gel permeation chromatography on a column [Sephadex LH-20, Pharmacia, 8 cm(dia.) ×60 cm], eluted with the same solvent. The fractions rich in dolichyl monophosphate as detected by TLC analysis were collected and concentrated under reduced pressure. TLC analysis showed that the dolichyl monophosphate obtained as above, weighing about 40 g, contained an impurity developed farther beyond dolichyl monophosphate on the chromatogram. Attempts were made to purify the dolichyl monophosphate by means of DEAEcellulose column chromatography and Sephadex LH-20 gel permeation chromatography but the impurity could not be completely eliminated from the dolichyl monophosphate.

EXAMPLE 1

A three-necked flask was charged with 10 ml (107 m mol) of phosphoryl chloride, and with stirring under ice-cooling, a solution of 20 g (15.3 m mol) of the same dolichol as used in Reference Example 1 and 3.2 ml (23 m mol) of triethylamine in 100 ml of THF was added thereto dropwise at 5 to 10° C. After completion of the addition, the reaction mixture was stirred under ice-cooling for 2 hours to give a dolichyl dichlorophosphate-containing reaction mixture To this reaction mixture was added 333 ml of 1 N aqueous sodium hydroxide solution dropwise under ice-cooling carefully below 10° C. After completion of the addition, the reaction mixture was further stirred at room temperature for 2 hours. The reaction mixture was extracted with 300 ml of chloroform three times (total: 900 ml). The organic layer was dried over anhydrous calcium chloride and the solvent was evaporated under reduced pressure to give crude dolichyl monophosphate. This crude product was submitted to column chromatography [column: DEAEcellulose, Whatman DE-52, acetate-form, 7.5 cm(dia.) × 50 cm; eluent: chloroform-methanol-water=20:10:1 (v/v); gradient: ammonium acetate from 0 to 30 mM]and the fractions containing dolichyl monophosphate alone as detected by TLC analysis are collected and concentrated under reduced pressure. The concentrate was suspended in chloroform and filtered with the aid of Florisil. The filtrate was concentrated to give 17 g of a pale yellow liquid. By the following spectrometric analyses, this liquid was confirmed to be dolichyl monophosphate. The yield from dolichol was 80%.

IR(cm$^{-1}$) ν (film): 1660, 1075, 830, 770

$^1$H-NMR δ $_{CDCl_3}^{ppm}$ (3H, d), 1.0-2.3 (131H) containing 1.53 (s) and 1.62 (s)], 3.90 (2H, dt), 5.06 (18H, br)

This product was analyzed on a semipreparative high performance liquid chromatographic column [Merck, Hibar LiChrosorb RP18 (5 μm, 250 mm ×4 mm dia.)-]with a 1:1 (v/v) mixture of isopropyl alcohol and methanol (10 mM phosphoric acid) as the eluent. The retention times of the dolichyl monophosphate homologs were found to be in complete agreement with those of the homologs in Sigma's commercial dolichyl monophosphate, respectively.

EXAMPLE 2

By the same reaction and separation procedures as described in Example 1 except that 333 ml of 1 N aqueous potassium hydroxide solution was used in lieu of 333 ml of 1 N aqueous sodium hydroxide solution, there was obtained 16.5 g of dolichyl monophosphate which showed substantially the same IR and NMR spectra as the dolichyl monophosphate obtained in Example 1. The yield from dolichol was 78%.

EXAMPLE 3

By the same reaction and separation procedures as described in Example 1 except that 333 ml of 1 N aqueous barium hydroxide solution was used in lieu of 333 ml of 1 N aqueous sodium hydroxide, there was obtained 16.3 g of dolichyl monophosphate which showed substantially the same IR and NMR spectra as the dolichyl monophosphate obtained in Example 1. The yield from dolichol was 77%.

EXAMPLE 4

By the same reaction and separation procedures as described in Example 1 except that 100 ml of DME was used in lieu of 100 ml of THF, there was obtained 16.8 g of dolichyl monophosphate which showed substantially the same IR and NMR spectra as the dolichyl monophosphate obtained in Example 1. The yield from dolichol was 79%.

EXAMPLE 5

By the same reaction and separation procedures as described in Example 1 except that 100 ml of DME was used in lieu of 100 ml of THF and 333 ml of 1 N aqueous potassium hydroxide solution in lieu of 1 N aqueous sodium hydroxide solution, there was obtained 16.0 g of dolichyl monophosphate which showed substantially the same IR and NMR spectra as the dolichyl monophosphate obtained in Example 1. The yield from dolichol was 75%.

EXAMPLE 6

By the same reaction and separation procedures as described in Example 1 except that 1.86 ml of pyridine was used in lieu of 3.2 ml of triethylamine, there was obtained 16.2 g of dolichyl monophosphate which showed substantially the same IR and NMR spectra as the dolichyl monophosphate obtained in Example 1. The yield from dolichol was 76%.

EXAMPLE 7

By the same reaction and separation procedures as described in Example 1, from 20 g of a dolichol of the general formula (II') wherein n means 15 was obtained 17.0 g of a dolichyl monophosphate of the general formula (I') wherein n is equal to 15 which showed substantially the same IR and NMR spectra as the dolichyl monophosphate obtained in Example 1. The yield from dolichol was 80%.

EXAMPLE 8

A three-necked flask was charged with 0.77 ml (8.3 m mol) of phosphoryl chloride and with stirring under ice-cooling, a solution of 1.0 g (2.8 m mol) of an α-dihydropolyprenol of the general formula (II) wherein m is equal to 4 and 0.6 ml (4.3 m mol) of triethylamine in 10 ml of THF was slowly added thereto dropwise at 5 to 10° C. After completion of the addition, the reaction mixture was stirred under ice-cooling for 2 hours to give an α-dihydropolyprenyl dichlorophosphate-containing reaction mixture. To this reaction mixture was added 25.2 ml of 1 N aqueous sodium hydroxide solution dropwise under ice-cooling carefully below 10° C. After completion of the addition, the reaction mixture was stirred at room temperature for 2 hours. The reaction mixture was extracted with 30 ml of chloroform three times (total: 90 ml). The organic layer was dried over anhydrous calcium chloride and the solvent was evaporated under reduced pressure to give crude α-dihydropolyprenyl monophosphate. This crude product was submitted to column chromatography [column: DEAE-cellulose, Whatman DE-52, acetate-form, 3.5 cm(dia.) ×12 cm; eluent: chloroform-methanol-water=20:10:1, v/v; gradient: ammonium acetate from 0 to 30 mM] and the fractions containing α-dihydropolyprenyl phosphate alone as detected by TLC analysis were collected and concentrated under reduced pressure. The concentrate was suspended in chloroform, filtered with the aid of Florisil, and concentrated to give 721 mg of a pale yellow liquid. This product was confirmed to be α-dihydropolyprenyl phosphate by the following spectrometric analyses. The yield from α-dihydropolyprenol was 59%.

IR(cm$^{-1}$) ν (film): 1670, 1075, 845, 770

$^1$H-NMR δ $_{CDCl_3}^{ppm}$: 0.85 (3H, d), 1.0–2.3 (34H) [containing 1.6 (s) and 1.7 (s)], 3.90 (2H, dt), 5.10 (4H, m), 8.10 (2H, br)

EXAMPLE 9

An argon-purged three-necked flask was charged with 10 ml (107 m mol) of phosphoryl chloride, and with stirring under ice-cooling, a solution of 20 g (15.3 m mol) of the same dolichol as used in Reference Example 1 and 3.2 ml (23 m mol) of triethylamine in 100 ml of THF was slowly added thereto dropwise at 5° to 10° C. After completion of the addition, the reaction mixture was stirred under ice-cooling for 2 hours. The solvent and the unreacted phosphoryl chloride and triethylamine were evaporated under reduced pressure. To the residue was added 50 ml of anhydrous ether and after thorough stirring, the mixture was filtered with the aid of Celite. The filtrate was concentrated under reduced pressure to give 21.9 g of a yellow liquid. IR spectrum of this yellow liquid showed no absorption attributable to the hydroxyl group of dolichol (3300 cm$^{-1}$) but showed characteristic absorptions of dolichyl dichlorophosphate (1300, 1285, 1025 and 985 cm$^{-1}$). $^1$H-NMR spectrum of the above yellow liquid showed the absence of the signal assignable to —CH$_2$OH of dolichol at δ 3.65 ppm (2H, t) and, instead, showed a signal assignable to —CH$_2$—OP(O)Cl$_2$ at δ 4.50 ppm (2H, dt). Based on the above spectrometric analyses, the above yellow liquid was identified to be dolichyl dichlorophosphate.

In 100 ml of THF was dissolved the dolichyl dichlorophosphate prepared above, and with stirring under ice-cooling, 333 ml of 1 N aqueous sodium hydroxide solution was added thereto dropwise carefully below 10° C. After completion of the addition, the reaction mixture was stirred at room temperature for 2 hours. Then, the reaction mixture was extracted with 300 ml of chloroform three times (total: 900 ml). The organic layer was dried over anhydrous calcium chloride and the solvent was evaporated under reduced pressure to give crude dolichyl monophosphate. This crude product was submitted to column chromatography [column: DEAE-cellulose, Whatman DE-52, acetate-form, 7.5 cm(dia.) ×50 cm; eluent: chloroform-methanol-water=20:10:1, v/v; gradient: ammonium acetate from 0 to 30 mM] and the fractions containing dolichyl monophosphate alone as detected by TLC analysis were collected and concentrated under reduced pressure. The concentrate was suspended in chloroform and filtered with the aid of Florisil, followed by concentration to give 17 g of a pale yellow liquid. By the following spectrometric analyses, this liquid was identified to be dolichyl monophosphate. The yield from dolichol was 80%.

IR(cm$^{-1}$) ν (film): 1660, 1075, 830, 770

$^1$H-NMR δ $_{CDCl_3}^{ppm}$: 0.92 (3H, d), 1.0–2.3 (131H) [containing 1.53 (s) and 1.62 (s)], 3.90 (2H, dt), 5.06 (18H, br)

This product was analyzed on a semipreparative high performance liquid chromatographic column [Merck, Hibar LiChrosorb RP18 (5 μm, 250 mm ×4 mm dia.)] with a 1:1 (v/v) mixture of isopropyl alcohol and methanol (1 mM phosphoric acid) as the eluent. The retention times of the dolichyl monophosphate homologs were found to be in complete agreement with those of the homologs in Sigma's commercial dolichyl monophosphate, respectively.

EXAMPLE 10

By the same reaction and separation procedures as described in Example 9 except that 100 ml of DME was used in lieu of 100 ml of THF, there was obtained 22.1 g of dolichyl dichlorophosphate which showed substantially the same IR and NMR spectra as the dolichyl dichlorophosphate obtained in Example 9.

By the same reaction and separation procedures as described in Example 9 except that 333 ml of 1 N aqueous potassium hydroxide solution was used in lieu of 33 ml of 1 N aqueous sodium hydroxide solution, from the dolichyl dichlorophosphate prepared above was obtained 16.5 g of dolichyl monophosphate, which showed substantially the same IR and NMR spectra as the dolichyl monophosphate obtained in Example 9. The yield from dolichol was 78%.

EXAMPLE 11

By the same reaction and separation procedures as described in Example 9 except that 1.86 ml of pyridine was used in lieu of 3.2 ml of triethylamine, there was obtained 21.7 g of dolichyl dichlorophosphate, which showed substantially the same IR and NMR spectra as the dolichyl dichlorophosphate obtained in Example 9.

The dolichyl dichlorophosphate thus obtained was converted by the same reaction and separation procedures as described in Example 9 to 16.4 g of dolichyl monophosphate. This product showed substantially the same IR and NMR spectra as the dolichyl monophosphate obtained in Example 9. The yield from dolichol was 77%.

EXAMPLE 12

By the same reaction and separation procedures as described in Example 9, from 20 g of a dolichol of the general formula (II') wherein n means 15 was obtained 22.2 g of a dolichyl dichlorophosphate of the general formula (I') wherein n means 15, which showed substantially the same IR and NMR spectra as the dolichyl dichlorophosphate obtained in Example 9.

By the same reaction and separation procedures as described in Example 9, from the dolichyl dichlorophosphate thus obtained was obtained 16.9 g of a dolichyl monophosphate of the general formula (III') wherein n means 15, which showed substantially the same IR and NMR spectra as the dolichyl monophosphate obtained in Example 9. The yield from dolichol was 80%.

EXAMPLE 13

A three-necked flask was charged with 0.77 ml (8.3 m mol) of phosphoryl chloride, and with stirring under ice-cooling, a solution of 1.0 g (2.8 m mol) of α-dihydropolyprenol of the general formula (II) wherein m means 4 and 0.6 ml (4.3 m mol) of triethylamine in 10 ml of THF was added thereto dropwise carefully at 5° to 10° C. After completion of the addition, the reaction mixture was stirred under ice-cooling for 2 hours to give an α-dihydropolyprenyl dichlorophosphate-containing reaction mixture. From this reaction mixture, the solvent and the unreacted phosphoryl chloride and triethylamine were evaporated under reduced pressure, and 50 ml of anhydrous ether was added to the residue. The mixture was stirred well and filtered with the aid of Celite. The filtrate was concentrated under reduced pressure to give 1.03 g of α-dihydropolyprenyl dichlorophosphate of the general formula (III) wherein m means 4.

In 10 ml of THF was dissolved the above α-dihydropolyprenyl dichlorophosphate, and under ice-cooling, 25.2 ml of 1 N aqueous sodium hydroxide solution was added thereto dropwise carefully below 10° C. After completion of the addition, the mixture was stirred at room temperature for 2 hours. The reaction mixture was then extracted with 30 ml of chloroform three times (total: 90 ml). The organic layer was dried over anhydrous calcium chloride and the solvent was evaporated under reduced pressure to give crude α-dihydropolyprenyl monophosphate. This crude product was submitted to column chromatography [column: DEAE-cellulose, Whatman DE-52, acetate-form, 3.5 cm(dia.) ×12 cm; eluent: chloroform-methanol-water=20:10:1, v/v; gradient: ammonium acetate from 0 to 30 mM]and the fractions containing α-dihydropolyprenyl monophosphate alone as detected by TLC analysis were collected and concentrated under reduced pressure. The concentrate was suspended in chloroform, filtered with the aid of Florisil, and concentrated to give 721 mg of a pale yellow liquid. By the following spectrometric analyses, this liquid was identified to be α-dihydropolyprenyl monophosphate. The yield from α-dihydropolyprenol was 59%.

IR(cm$^{-1}$) ν (film): 1670, 1075, 845, 770
$^1$H-NMR δ $_{CDCL_3}^{ppm}$: 0.85 (3H, d), 1.0–2.3 (34H), [containing 1.6 (s) and 1.7 (s)],
3.90 (2H, dt), 5.10 (4H, m),
8.10 (2H, br)

REFERENCE EXAMPLE 2

An argon-purged three-necked flask was charged with 240 μl of phosphoryl chloride and the content was stirred in an ice-methanol bath. To this phosphoryl chloride was slowly added dropwise a THF solution of 0.99 g (0.76 m mol) of the same dolichol as that used in Reference Example 1 and 180 μl of triethylamine. After completion of the addition, the reaction mixture was stirred for 1 hour and the solvent and the excess phosphoryl chloride and triethylamine were evaporated under reduced pressure. The residue was suspended in ether and filtered. The filtrate was concentrated under reduced pressure. The concentrate was diluted with 10 ml of THF. Separately, 300 mg (0.85 m mol) of 2,3,4,6-tetra-O-acetyl-β-D-glucopyranose was dissolved in 3 ml of THF and the solution was stirred under argon atmosphere at −70° C. To this solution was added 0.47 ml of 1.82 N solution of n-butyllithium in hexane, followed by addition of the dichlorophosphate solution prepared above and 0.15 ml of HMPA, and the mixture was stirred at −70 °to −60°C. overnight. The reaction mixture was poured into water, the organic layer was separated, and the aqueous layer was extracted with ether. The organic layers were collected and dried over anhydrous sodium sulfate and the solvent was distilled off under reduced pressure. The residue was submitted to silica gel chromatography [Merck, Art. 7734, Kieselgel 60, 70–230 mesh, 120 g; eluent: chloroform-methanol-28% aqueous ammonia=80:20:1, v/v]to give 604 mg of dolichyl 2,3,4,6-tetra-O-acetyl-D-glucopyranosyl chlorophosphate. The yield from dolichol was 47%.

IR(cm$^{-1}$) ν (film): 1755, 1665, 1230, 985, 840, 750
$^1$H-NMR δ ppm : 0.92 (3H), 1.0–2.3 (144H),
3.7–5.8 (27H)

In 15 ml of THF was dissolved the above dolichyl 2,3,4,6-tetra-O-acetyl-D-glucopyranosyl chlorophosphate, and with stirring under ice-cooling, 7.3 ml of 0.2 N aqueous sodium hydroxide solution was added thereto. The mixtuxe was stirred at room temperature for 4 hours. The organic layer was separated, and the aqueous layer was extracted with ether The organic layers were collected and dried over anhydrous sodium sulfate. Then, the solvent was distilled off under reduced pressure to give dolichyl 2,3,4,6-tetra-O-acetyl-D-glucopyranosyl phosphate. This product was dissolved in chloroform and a 1% solution of sodium methoxide in methanol was added until the pH of the mixture became 12. The mixture was stirred at room temperature for 1 hour. The reaction mixture was then neutralized with an ion exchange resin [Bio-Rad, AG 50W-X8, 200–400 mesh, pyridinium-form]and filtered and the solvent was evaporated under reduced pressure. The residue was submitted to silica gel column. chromatography [Merck, Art. 7734, Kieselgel 60, 70–230 mesh; eluent: chloroformmethanol-28% aqueous ammonia=75:25:1, v/v]to give 358 mg of dolichyl D-glucopyranosyl phosphate. The yield from chlorophosphate was 65%.

IR(cm$^{-1}$) ν (film): 3350, 1665, 1230, 985, 840, 750
$^1$H-NMR δ ppm : 0.92 (3H), 1.0–2.3 (132H),
3.2–5.8 (27H)

REFERENCE EXAMPLE 3

By the same reaction and separation procedures as described in Reference Example 2, from 300 mg of 2,3,4,6-tetra-O-acetyl-β-D-mannopyranose was obtained 624 mg of dolichyl 2,3,4,6-tetra-O-acetyl-D-mannopyranosyl phosphate. The yield from dolichol was 49%.

IR(cm$^{-1}$) ν (film): 1755, 1665, 1230, 985, 840, 750
$^1$H-NMR δ ppm : 0.92 (3H), 1.0–2.3 (144H),
3.7–5.8 (27H)

REFERENCE EXAMPLE 4

By the same reaction and separation procedures as described in Reference Example 2, from 500 mg of 2,3,4,6-tetra-O-benzoyl-β-D-glucopyranose was obtained 663 mg of dolichyl 2,3,4,6-tetra-O-benzoyl-D-glucopyranosyl phosphate. The yield from dolichol was 46%.

IR(cm$^{-1}$) ν (film): 1730, 1665, 1600, 1500, 1230, 985, 840, 750

$^1$H-NMR δ ppm : 0.92 (3H), 1.0–2.3 (132H), 3.7–5.8 (27H), 7.5–8.2 (20H)

REFERENCE EXAMPLE 5

By the same reaction and separation procedures as described in Reference Example 2, from 450 mg of 2,3,4,6-tetra-O-benzyl-D-glucopyranose was obtained 675 mg of dolichyl 2,3,4,6-tetra-O-benzyl-D-glucopyranosyl phosphate. The yield from dolichol was 47%.

IR(cm$^{-1}$) ν (film): 1665, 1600, 1500, 1230, 985, 840, 750

$^1$H-NMR δ ppm : 0.92 (3H), 1.0–2.3 (132H), 3.7–5.8 (35H), 7.2 (20H)

The phosphate obtained above was dissolved in 3 ml of THF and cooled to −50° C. To the solution was added 30 ml of ethylamine, followed by addition of 120 mg of lithium metal at −30° to −20° C. and the mixture was stirred at the same temperature for 2 hours. To the reaction mixture was added 2 ml of ethanol and the ethylamine was evaporated at room temperature. To the residue was added water, followed by extraction with chloroform. The organic layer was washed with water and dried over anhydrous sodium sulfate. The solvent was then evaporated and the residue was submitted to silica gel column chromatography [Merck, Art. 7734, Kieselgel 60, 70–230 mesh; eluent: chloroform-methanol-28% aqueous ammonia=75:25:1, v/v] to give 178 mg of dolichyl D-glucopyranosyl phosphate, which showed substantially the same IR and NMR spectra as the dolichyl D-glucopyranosyl phosphate obtained in Reference Example 2. The yield based on the phosphate was 29%.

REFERENCE EXAMPLE 6

By the same reaction and separation procedures as described in Reference Example 2, from 300 mg of 2-deoxy-3,4,6-tri-O-acetyl-D-glucopyranose was obtained 598 mg of dolichyl 2-deoxy-3,4,6-tri-O-acetyl-D-glucopyranosyl phosphate. The yield from dolichol was 48%.

IR(cm$^{-1}$) ν (film): 1755, 1665, 1230, 985, 840, 750

$^1$H-NMR δ ppm : 0.92 (3H), 1.0–2.3 (142H), 3.7–5.8 (27H)

REFERENCE EXAMPLE 7

By the same reaction and separation procedures as described in Reference Example 2, from 300 mg of 2-deoxy-2-acetamido-3,4,6-tri-O-acetyl-D-glucopyranose was obtained 620 mg of dolichyl 2-deoxy-2-acetamido-3,4,6-tri-O-acetyl-D-glucopyranosyl phosphate. The yield from dolichol was 46%.

IR(cm$^{-1}$) ν (film): 1755, 1655, 1530, 1230, 985, 840, 750

$^1$H-NMR δ ppm : 0.92 (3H), 1.0–2.3 (144H),

REFERENCE EXAMPLE 8

By the same reaction and separation procedures as described in Reference Example 2, from 0.51 g of dolichol of the general formula (II') wherein n means 6 was obtained 266 mg of dolichyl 2,3,4,6-tetra-O-acetyl-D-glucopyranosyl phosphate [dolichyl glycopyranosyl phosphate of the general formula (VI) wherein m means 9]. The yield from dolichol was 27%.

IR(cm$^{-1}$) ν (film): 1755, 1665, 1230, 985, 840, 750

$^1$H-NMR δ ppm : 0.92 (3H), 1.0–2.3 (81H), 3.7–5.8 (18H)

REFERENCE EXAMPLE 9

By the same reaction and separation procedures as described in Reference Example 2, from 0.30 g of dolichol of the general formula (II') wherein n means 1 was obtained 240 mg of dolichyl 2,3,4,6-tetra-O-acetyl-D-glucopyranosyl phosphate [dolichyl glycopyranosyl phosphate of the general formula (VI) wherein m means 4]. The yield from dolichol was 29%.

IR(cm$^{-1}$) ν (film): 1755, 1665, 1230, 985, 840, 750

$^1$H-NMR δ ppm : 0.92 (3H), 1.0–2.3 (56H), 3.7–5.8 (13H)

REFERENCE EXAMPLE 10

By the same reaction and separation procedures as described in Reference Example 2, from 300 mg of dolichol of the general formula (II') wherein n means 15 was obtained 601 mg of dolichyl 2,3,4,6-tetra-O-acetyl-D-glucopyranosyl chlorophosphate [dolichyl glycopyranosyl phosphate of the general formula (VI) wherein m means 18], which showed substantially the same IR and NMR spectra as the dolichyl 2,3,4,6-tetra-O-acetyl-D-glucopyranosyl phosphate obtained in Reference Example 2. The yield from dolichol was 47%.

REFERENCE EXAMPLE 11

An argon-purged three-necked flask was charged with 240 μl of phosphoryl chloride and the content was stirred in an ice-methanol bath. To this phosphoryl chloride was slowly added dropwise a THF solution of 0.99 g (0.76 m mol) of the same dolichol as that used in Reference Example 2 and 180 μl of triethylamine. After completion of the addition, the reaction mixture was stirred for 1 hour and the solvent and the excess phosphoryl chloride and triethylamine were evaporated under reduced pressure The residue was suspended in ether and after filtration to remove the insoluble matter, the filtrate was concentrated under reduced pressure The concentrate was diluted with 10 ml of THF to give a dichlorophosphate solution. Separately, 300 mg (0.85 m mol) of 2,3,4,6-tetra-O-acetyl-β-D-glucopyranose was dissolved in 3 ml of THF and the solution was stirred under argon atmosphere at −70° C. To the solution was added 0.47 ml of 1.82 N solution of n-butyllithium in hexane, followed by addition of the dichlorophosphate solution prepared above and 0.15 ml of HMPA and the mixture was stirred at −70 to −60° C. overnight. To the reaction mixture was added 7.4 ml of 0.2 N aqueous sodium hydroxide solution and the mixture was stirred at room temperature for 4 hours. The organic layer was separated and the aqueous layer was extracted with ether. The organic layers were collected and dried over anhydrous sodium sulfate and the solvent was evaporated under reduced pressure. The residue was submitted to silica gel chromatography [Merck, Art. 7734, Kieselgel 60, 70–230 mesh, 120 g;

eluent: chloroform-methanol-28%, aqueous ammonia=80:20:1, v/v]to give 621 mg of dolichyl 2,3,4,6-tetra-O-acetyl-D-glucopyranosyl phosphate. The yield from dolichol was 48%.

IR(cm$^{-1}$) $\nu$ (film): 1755, 1665, 1230, 985, 840, 750

$^1$H-NMR $\delta$ ppm : 0.92 (3H), 1.0–2.3 (144H), 3.7–5.8 (27H)

In 5 ml of chloroform was dissolved the above dolichyl 2,3,4,6-tetra-O-acetyl-D-glucopyranosyl phosphate and a 1% solution of sodium methoxide in methanol was added until the pH of the reaction mixture became 12. The mixture was stirred at room temperature for 1 hour. The reaction mixture was then neutralized with an ion exchange resin [Bio-Rad, AG 50W-X8, 200-400 mesh, pyridinium-form]and filtered and the solvent was evaporated under reduced pressure. The residue was submitted to silica gel column chromatography [Merck, Art. 7734, Kieselgel 60, 70–230 mesh; eluent: chloroform-methanol-28% aqueous ammonia=75:25:1, v/v]to give 376 mg of dolichyl D-glucopyranosyl phosphate. The yield from phosphate was 67%.

IR(cm$^{-1}$) $\nu$ (film): 3350, 1665, 1230, 985, 840, 750

$^1$H-NMR $\delta$ ppm : 0.92 (3H), 1.0–2.3 (132H), 3.2–5.8 (27H)

REFERENCE EXAMPLE 12

An argon-purged two-necked flask was charged with 229 mg (1.49 m mol) of phosphoryl chloride and 1 ml of ether and the content was stirred at −50° C. A solution of 1.95 g (1.48 m mol) of the same dolichol as that used in Reference Example 2 and 154 mg (1.52 m mol) of triethylamine in 1 ml of ether was added thereto dropwise. After completion of the addition, the mixture was further stirred for 3 hours at −30° C., then warmed to room temperature. The insoluble material was filtered off and the filtrate was concentrated under reduced pressure. TLC analysis revealed that the dolichol remained. The residue was dissolved in 5 ml of THF and under ice-cooling, 3 ml of 1 N aqueous sodium hydroxide solution was added thereto dropwise, and the mixture was stirred at room temperature overnight. The mixture was diluted with water and extracted with chloroform three times. The organic layer was dried over anhydrous calcium chloride and the solvent was distilled off under reduced pressure to give 2.49 g of a pale yellow oily material. TLC analysis revealed that the material was a mixture of several compounds including dolichol. By the following NMR spectrum, it was found that about 50% of dolichol was phosphorylated. And TLC analysis confirmed that the phosphorylated compound consisted of several compounds.

$^1$H-NMR $\delta$ $_{CDCl_3}^{ppm}$ (3H, d), 1.0–2.3 (131H), 3.90 (ca. 1H, br), 5.06 (18H, br)

What is claimed is:

1. A method of producing an α-dihydropolyprenyl monophosphate of the general formula

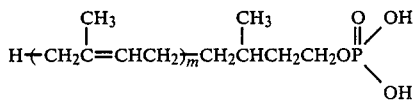

wherein m is an integer of 4 to 22 which comprises hydrolyzing an α-dihydropolyprenyl dichlorophosphate of the general formula

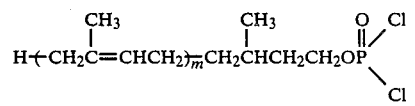

wherein m is as defined above with an alkali metal hydroxide or alkaline earth metal hydroxide in an ethereal solvent.

2. The method of claim 1 wherein the ethereal solvent is tetrahydrofuran, 1,2-dimethoxyethane or diethyl ether.

3. The method of claim 1 wherein the amount of ethereal solvent is about 2 times to about 100 times by weight based on the α-dihydropolyprenyl dichlorophosphate.

4. The method of claim 1 wherein the amount of the alkali metal hydroxide or alkaline earth metal hydroxide is about 2 molar equivalents to about 10 molar equivalents per mole of the α-dihydropolyprenyl dichlorophosphate.

5. The method of claim 1 wherein the reaction is carried out at temperatures of about 0° C. to about 10° C.

* * * * *

UNITED STATES PATENT AND TRADEMARK OFFICE
CERTIFICATE OF CORRECTION

PATENT NO. : 4,792,615
DATED : December 20, 1988
INVENTOR(S) : Nakagawa et al

It is certified that error appears in the above-identified patent and that said Letters Patent is hereby corrected as shown below:

Column 7, Line 67, change "2imidazolidinone" to --2-imidazolidinone--.

Column 13, Line 54, change "985 cm$^{31}$ $^{1}$)" to --985 cm$^{-1}$)--.

Column 15, Line 58, change "CDCL$_3$" to --CDCl$_3$--.

Signed and Sealed this

Second Day of January, 1990

Attest:

JEFFREY M. SAMUELS

Attesting Officer     Acting Commissioner of Patents and Trademarks